(12) United States Patent
Martin

(10) Patent No.: US 8,946,486 B2
(45) Date of Patent: Feb. 3, 2015

(54) METHOD OF FORMING ALKOXYLATED FLUOROALCOHOLS

(75) Inventor: Thomas Joseph Martin, Mansfield, TX (US)

(73) Assignee: Tyco Fire & Security GmbH, Neuhausen am Rheinfall (CH)

( * ) Notice: Subject to any disclaimer, the term of this patent is extended or adjusted under 35 U.S.C. 154(b) by 58 days.

(21) Appl. No.: 12/325,329

(22) Filed: Dec. 1, 2008

(65) Prior Publication Data

US 2009/0143621 A1 Jun. 4, 2009

Related U.S. Application Data

(60) Provisional application No. 60/991,982, filed on Dec. 3, 2007.

(51) Int. Cl.
| | |
|---|---|
| *C07C 41/03* | (2006.01) |
| *C07C 43/12* | (2006.01) |
| *C07C 303/40* | (2006.01) |
| *C07C 231/12* | (2006.01) |

(52) U.S. Cl.
CPC ............... *C07C 303/40* (2013.01); *C07C 41/03* (2013.01); *C07C 231/12* (2013.01)
USPC ........................................ 568/615

(58) Field of Classification Search
CPC ....................................... C07C 41/03
USPC ....................................... 568/615
See application file for complete search history.

(56) References Cited

U.S. PATENT DOCUMENTS

| | | | |
|---|---|---|---|
| 2,600,378 A * | 6/1952 | Dickey et al. ................. | 558/127 |
| 2,723,999 A | 11/1955 | Cowanet al. | |
| 3,359,331 A | 12/1967 | Baker et al. | |
| 3,676,477 A | 7/1972 | Chay et al. | |
| 3,944,586 A | 3/1976 | Knowles | |
| 3,944,653 A | 3/1976 | Stewart et al. | |
| 3,948,668 A | 4/1976 | Hayek et al. | |
| 3,980,715 A | 9/1976 | Szur | |
| 4,169,104 A | 9/1979 | Burt et al. | |
| 4,240,956 A | 12/1980 | Weil et al. | |
| 4,287,118 A | 9/1981 | Muldrow, Jr. | |
| 4,408,043 A | 10/1983 | Seale et al. | |
| 4,456,697 A | 6/1984 | Yang | |
| 4,483,941 A | 11/1984 | Yang | |
| 4,490,561 A | 12/1984 | Yang et al. | |
| 4,594,200 A | 6/1986 | Penny | |
| 4,983,778 A | 1/1991 | Ploog | |
| 4,992,211 A | 2/1991 | Casciani | |
| 5,041,576 A | 8/1991 | Wasfi | |
| 5,057,628 A | 10/1991 | Edwards et al. | |
| 5,210,323 A | 5/1993 | Wimmer et al. | |
| 5,290,912 A | 3/1994 | Watabe et al. | |
| 5,567,857 A | 10/1996 | Huang et al. | |
| 5,608,116 A | 3/1997 | Halling et al. | |
| 5,852,148 A | 12/1998 | Behr et al. | |
| 5,910,599 A | 6/1999 | Tanaka et al. | |
| 6,028,230 A | 2/2000 | Le-Khac et al. | |
| 6,048,952 A | 4/2000 | Behr et al. | |
| 6,201,101 B1 | 3/2001 | Tozzola et al. | |
| 6,340,779 B1 | 1/2002 | Enna et al. | |
| 6,365,541 B1 | 4/2002 | Wimmer et al. | |
| 6,365,769 B1 | 4/2002 | Behr et al. | |
| 6,395,083 B2 | 5/2002 | Enna et al. | |
| 6,455,459 B1 | 9/2002 | Bedard et al. | |
| 6,734,327 B2 | 5/2004 | Bedard et al. | |
| 2004/0266981 A1 | 12/2004 | Yokoyama et al. | |
| 2006/0069220 A1 * | 3/2006 | Meurs et al. .................. | 526/160 |

FOREIGN PATENT DOCUMENTS

| | | | | |
|---|---|---|---|---|
| DE | 111522 A | * | 2/1975 | .............. C07C 43/12 |
| GB | 1 410 328 | * | 10/1975 | .............. C08G 65/28 |
| JP | 2005-046749 | | 2/2005 | |
| SU | 570590 A | * | 9/1977 | .............. C07C 43/12 |

OTHER PUBLICATIONS

Michael Briggs, "Boron Oxides, Boric Acid, and Borates", Kirk-Othmer Encyclopedia of Chemical Technology, vol. 4, published online Jul. 2001, pp. 241-294.*
Young, D.E., et al., Perfluoroalkyl Borate Esters from Reactions with Boron Trichloride, Inorganic Chemistry, 1971, pp. 2810-2812,vol. 10, No. 12.
Landesman, H., et al., Fluoroalkyl Borate Esters, Inorganic Chemistry, Jun. 1967, pp. 896-898, vol. 3, No. 6.
DuPont Zonyl FSH Fluorosurfactant Product Sheet, 2001, pp. 1-2.
DuPont Zonyl FSN-100 Fluorosurfactant Product Sheet, 2005, pp. 1-2.
DuPont Zonyl FSO Fluorosurfactant Product Sheet, 2005, pp. 1-2.

* cited by examiner

*Primary Examiner* — Rosalynd Keys
(74) *Attorney, Agent, or Firm* — Perkins Coie LLP

(57) ABSTRACT

A method of forming an alkoxylated fluoroalcohol is accomplished by providing a boron compound having or providing at least one boron-oxygen bond and an iodine source. The boron compound and iodine source are combined with reactants of a fluoroalcohol and an alkylene oxide in the presence of a base. The reactants are allowed to react to form an alkoxylated fluoroalcohol reaction product.

9 Claims, No Drawings

METHOD OF FORMING ALKOXYLATED FLUOROALCOHOLS

CROSS-REFERENCE TO RELATED APPLICATIONS

This application claims the benefit of U.S. Provisional Application No. 60/991,982, filed Dec. 3, 2007, which is incorporated herein by reference in its entirety.

BACKGROUND

Hydrocarbon surfactants are very common and are the workhorse materials for making aqueous foams and wetting surfaces, among other things. Surfactants, in general, produce these effects by lowering the surface tension of the liquid in which they are dissolved. Hydrocarbon surfactants, however, lower the surface tension of water to only about 30 dynes/cm (0.03 N/m). To provide lower surface tensions, fluorosurfactants are often used.

Fluorosurfactants, including amphiphilic fluoropolymers, can give surface tensions of less than 20 dynes/cm (0.02 N/m), which are necessary to better wet low energy surfaces, for example. Like hydrocarbon surfactants, fluorosurfactants can be classified as anionic (containing negative charge), cationic (containing positive charge)), amphoteric (having both positive and negative charges) and nonionic (having no charge). Nonionic fluorosurfactants are particularly desirable due, not only to the very low surface tension obtainable, but also to their efficacy in extreme conditions such as high acidity or alkalinity, high salt levels (ionic strength), elevated temperatures, etc. They are also very resilient and not easily degraded.

One type of nonionic fluorosurfactant is an alkoxylated fluoroalcohol. The fluoroalcohol molecule itself is hydrophobic so that it is insoluble in water or other aqueous fluids. Alkoxylation of the fluoroalcohol adds a hydrophilic portion to the molecule so that it is water soluble and surface active.

Alkylene oxides, such as ethylene oxide and propylene oxide, are reactive toward most hydroxyl functional groups such as the terminal -OH of the fluoroalcohol or alkoxylated fluoroalcohol. In many cases, however, catalysts are employed to aid in the alkoxylation reaction. Existing catalysts for alkoxylating fluoroalcohols include boron trifluoride ($BF_3$ or $BF_3$-etherate), borohydrides, etc. These materials have certain shortcomings, however. Boron trifluoride is both toxic and corrosive and presents a safety and handling concern. Furthermore, it has a fairly low reactivity, broad alkoxylate distributions and requires excessive residual starting materials. Boron trifluoride also produces undesirable by-products, namely, HF and 1,4-dioxane. Borohydride catalysts for alkoxylation of fluoroalcohols are effective, but only with the addition of other additives, and are sensitive to impurities. Without the proper balance of additives and low impurities, borohydride catalysis for alkoxylating fluoroalcohols can be slow or fail outright. Borohydrides also present a handling and safety concern, because the borohydride powders are highly flammable and produce highly flammable hydrogen gas as a reaction byproduct.

There is therefore a need to provide a method of alkoxylating fluoroalcohols that overcomes these disadvantages of borohydride and boron trifluoride catalyst materials.

SUMMARY

A method of forming an alkoxylated fluoroalcohol is accomplished by combining a boron compound having or providing at least one boron-oxygen bond and an iodine source. These are provided with reactants of a fluoroalcohol and an alkylene oxide in the presence of a base. The reactants are allowed to react to form an alkoxylated fluoroalcohol reaction product.

In certain embodiments, the boron compound, which may provide three (3) boron-oxygen bonds, is an oxide of boron, an alkyl borate, a boric acid, a boric acid anhydride, a boronic acid, a borinic acid or salts or esters of said acids or combinations of these. These may include boric acid ($H_3BO_3$), a boric acid anhydride, meta boric acid ($HBO_2$), tetra boric acid ($H_2B_4O_7$), boron oxide ($B_2O_3$), trimethyl borate, triethyl borate, triisopropyl borate, tripropyl borate, tributyl borate, sodium tetraborate, potassium tetraborate or combinations of these. The boron compound may be used in an amount of from about 0.01 mole % to about 20 mole % by total moles of fluoroalcohol.

The iodine source may be selected from at least one of lithium iodide, sodium iodide, potassium iodide, calcium iodide, ammonium iodide, elemental iodine or combinations of these. In certain embodiments, the iodine source may be used in an amount of from about 0.05% to about 10% by weight of the fluoroalcohol.

The fluoroalcohol may have the structure of $F(CF_2)_m$—OH or $F(CF_2)_m$-A-OH, wherein m is from 2 to 20 and A is a

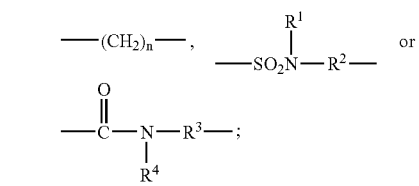

where n is from 1 to 6, $R^1$ and $R^4$ are each independently selected from one of hydrogen, a halogen or an alkyl group containing from 1-30 carbon atoms, and $R^2$ and $R^3$ are each independently selected from an alkylene group containing from 2 to 30 carbon atoms.

The alkylene oxide may have the structure:

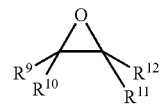

where $R^9$, $R^{10}$, $R^{11}$ and $R^{12}$ are each independently one of hydrogen, an alkyl group, an alkyl alcohol, an alkyl halide or an allyl ether. The alkylene oxide is used in an amount of from about 1 mole % to about 100 mole % by total moles of the fluoroalcohol and boron compound.

In certain embodiments the boron compound is initially combined with a non-fluoroalcohol that is subsequently substituted with the fluoroalcohol.

DETAILED DESCRIPTION

It has been discovered that certain less hazardous materials can be used to form boron catalyst systems having the same functionality as those boron trifluoride or borohydride catalysts previously described in forming alkoxylated fluoroalcohols.

It should be noted from the outset that the description and examples are presented herein solely for the purpose of illustrating various embodiments of the invention and should not be construed as a limitation to the scope and applicability of the invention. While the methods and compositions of the present invention are described herein as utilizing or comprising certain materials, it should be understood that the method or composition could optionally comprise two or more chemically different materials. In addition, the composition can also comprise some components other than the ones cited. In the summary and detailed description, each numerical value should be read once as modified by the term "about" (unless already expressly so modified), and then read again as not so modified unless otherwise indicated in context. Also, in the summary and description, it should be understood that a concentration, value or amount listed or described as being useful, suitable, or the like, is intended that any and every concentration, value or amount within the range, including the end points, is to be considered as having been stated. For example, "a range of from 1 to 10" is to be read as indicating each and every possible number along the continuum between about 1 and about 10. Thus, even if specific data points within the range, or even no data points within the range, are explicitly identified or refer to only a few specific, it is to be understood that the inventor appreciates and understands that any and all data points within the range are to be considered to have been specified, and that the inventor is in possession of the entire range and all points within the range.

In forming alkoxylated fluoroalcohols in accordance with the invention, the fluoroalcohol may be a fluoroalcohol having the generalized structure according to Equations (1) or (2) below:

$$F(CF_2)_m\text{—OH} \qquad (1)$$

$$F(CF_2)_m\text{-A-OH} \qquad (2)$$

where $F(CF_2)_m$ denotes a perfluorinated alkyl group, where m is usually, but not necessarily, 2-20, and more typically 4-14. In certain embodiments m may be from 2 to 8, and in still other embodiments m may be from 2 to 6. The alkyl group $F(CF_2)_m$ is typically linear but may be branched, as well. The linking group A may be a connecting group of a —$(CH_2)_n$—, which may be branched or linear,

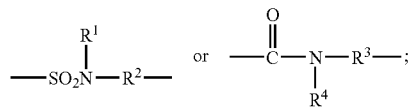

where n is from 1 to 6 or more, $R^1$ and $R^4$ are each independently selected from one of hydrogen, a halogen or an alkyl group containing from 1-30 carbon atoms, and $R^2$ and $R^3$ are each independently selected from an alkylene group containing from 2 to 30 carbon atoms. Typically, the linking group A is methylene or ethylene. In certain embodiments, the fluoroalcohol may include one or more hydrogens substituted for fluorine, such as the group $H(CF_2)_m$ for example. The fluoroalcohols may have molecular weights of from about 200 to about 2000 g/mol, more typically from about 300 to about 500 g/mol. Non-limiting examples of suitable fluoroalcohols are those described in U.S. Pat. Nos. 4,490,561; 5,590,561 and 5,608,116, which are each incorporated herein by reference in their entireties for all purposes.

The alkoxylating reaction is carried out using a catalyst system that includes a boron compound. Most alkoxylating agents are not appreciably soluble in the fluoroalcohols. The boron compound may complex with the alkoxylating agent facilitating incorporation and reaction of the alkoxylating agent with the fluoroalcohol. The catalyst or catalytic properties of the boron compound may be formed or provided in-situ, with the same or similar functionality as borohydride or boron trifluoride catalysts. As used herein, "in-situ" refers to the formation of the catalyst in the presence of the fluoroalcohol or at least one of the reactants. The boron compound is one that has or provides at least one boron-oxygen bond. In particular, the boron compound may have or provide one (1) to four (4) boron-oxygen bonds per boron atom. To produce a boron-based catalyst, the boron compound may be added to the fluoroalcohol or a stand-in alcohol to provide or create a catalyst species capable of carrying out the alkoxylating reactions. The boron compound may have, but is not limited to, the general structure shown in Equation (3) below:

where $R^5$ and $R^6$ are each independently H, an alkyl group (e.g. $CH_3$, $CH_3CH_2$, etc.), an aryl, an alkylaryl, an alkyl halide, a halogen (e.g. F, Cl, Br, I), or —$OR^8$, and wherein $R^7$ and $R^8$ are each independently H, an alkyl group, a carbonyl, a carboxyl, an aryl or an alkylaryl. While the boron compound of Equation 3 is shown as having three substituents, the boron compound also has an empty orbital that can complex with a fourth molecule, which is typically neutral or uncharged. This fourth molecule may include an alcohol, such as methanol, ethanol, etc., or an ether, such as diethyl ether, tetrahydrofuran, etc.

The boron compound may an oxide of boron, an alkyl borate, a boric acid, a boric acid anhydride, a boronic acid, a borinic acid or salts or esters of said acids or combinations of these. Examples of the boron compound may include boric acid ($H_3BO_3$), meta boric acid ($HBO_2$), tetra boric acid ($H_2B_4O_7$), boron oxide ($B_2O_3$), trimethyl borate, triethyl borate, triisopropyl borate, tripropyl borate, tributyl borate, and tetraborate salts, such sodium tetraborate (borax), potassium tetraborate, etc. Generally, any oxide, acid, salt or ester of boron may be useful in the present invention. Further examples of suitable boron compounds are described in U.S. Patent Application Publication No. 2006/0069220A1, which is herein incorporated by reference for all purposes. Examples of boric acid esters are described in Boric Acid Esters, Kirk-Othmer Encyclopedia of Chemical Technology, pp. 1-10, John Wiley & Sons, Inc., which is herein incorporated by reference. In certain instances, the boron compound may provide the boron-oxygen bond in-situ.

The boron compound may be used in an amount of from about 0.01 mole % to about 20 mole % by total moles of fluoroalcohol, more particularly from about 0.05 mole % to about 5 mole % by total moles of fluoroalcohol.

An iodine co-catalyst is also used in the catalyst system. The iodine co-catalyst is provided from an iodine source, which may be an alkali metal iodide, alkaline earth metal iodide or elemental iodine and combinations of these. Generally, all iodine salts may be useful as the iodine source. Examples of suitable iodine sources include lithium iodide, sodium iodide, potassium iodide, calcium iodide, ammonium iodide, elemental iodine or combinations of these. The iodine source is used in an amount of from about 0.05% to about 10% by weight of the fluoroalcohol, more particularly from about 0.1% to about 2% by weight of the fluoroalcohol. If the iodine source is other than sodium iodide (NaI) or elemental iodine (12), higher amounts of the iodine source may be used. In certain instances, approximately twice as much of the other iodine sources may be used. Thus, for example, if sodium iodide or elemental iodine are typically used in an amount of from about 0.05% to about 5% by weight of the fluoroalcohol, other iodine sources may be used in amounts of from about 0.1% to 10% by weight of the fluoroalcohol for the alkoxylation of the fluoroalcohol.

An alkoxylating agent of an alkylene oxide used for the fluoroalcohol alkoxylation may have the general structure of Equation (4) below:

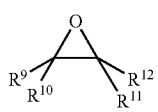
(4)

where $R^9$, $R^{10}$, $R^{11}$ and $R^{12}$ are each independently one of hydrogen, an alkyl group, an alkyl alcohol, an alkyl halide, an aryl, an alkylaryl or an allyl ether. Particularly useful are those alkylene oxides of ethylene oxide, propylene oxide, butylene oxide, glycidol, epichlorohydrin, styrene oxide, oxetane, tetrahydrofuran, 1,4-dioxane, allyl glycidyl ether, fluorinated cyclic ethers (e.g., fluorinated ethylene oxide, fluorinated propylene oxide, etc.) or mixtures of these. Ethylene oxide and propylene oxide are particularly useful in carrying out the alkoxylation reactions. Examples of suitable alkylene oxides for use in the alkoxylation reactions are described in U.S. Patent Application Publication No. 2006/0069220A1 and U.S. Pat. No. 5,608,116, which are each incorporated herein by reference.

The alkoxylating agent may be used in an amount of from about 1 mole % to about 100 mole % by total moles of the fluoroalcohol, more typically from about 2 mole % to about 20 mole %, and still more typically from about 3 mole % to about 12 mole % by total moles of the fluoroalcohol. The alkoxylating agent may be used in stoichiometric amounts to provide the desired degree of alkoxylation.

An alkali or base is also used in the reaction. While not wanting to be bound by any particular theory, it is believed that the base deprotonates the fluoroalcohol to allow it to react with the boron compound to form a borate ester in situ. Examples of suitable bases include metal hydroxides, such sodium hydroxide (NaOH), sodium hydride (NaH), and those having the general structure R—O—Na, where R is an alkyl, such as sodium methylate, sodium ethoxide, etc. Other bases may include KOH, $Ca(OH)_2$, $Mg(OH)_2$, etc., however, NaOH has been shown to work particularly well in testing. The base may be used in an amount of 0.05% to about 5% by weight of the fluoroalcohol, more particularly from about 1% to about 5% by weight of the fluoroalcohol.

In certain instances the reaction can be carried out under an inert atmosphere (nitrogen, argon, etc.) or in air. The reaction can also be carried out under a reduced pressure or under vacuum or under reactant pressure (e.g., ethylene oxide vapor pressure).

Although not necessary, solvents may be combined with the fluoroalcohol in certain instances, such as for temperature control and to facilitate solubility of the catalyst system, reactants or reaction products. Examples of suitable solvents include, polar and non-polar aprotic solvents such as dimethyl sulfoxide, N-methyl pyrrolidone, N,N-dimethyl formamide, glyme, diglyme, etc., acetone, acetonitrile, hydrocarbons, glycol ether esters, esters, fluorocarbon solvents, etc. Water is generally excluded from alkoxylation reactions by a drying process due to its initiation of unwanted, homo-polymerization.

To carry out the alkoxylating reaction, the iodine source and any base may be initially added to the fluoroalcohol. When added to the fluoroalcohol, NaOH and other bases may form water. It may be desirable to remove such water from the fluoroalcohol prior to adding the boron compound. Water may compete against the fluoroalcohol and react with the boron compound to produce unwanted side products or suboptimal catalytic species, or hamper the desired in situ catalyst formation. It may be desirable to therefore add the NaOH or other base prior to the salts and other components for this reason as well. The solution may then be heated to remove any water to dry the fluoroalcohol. The iodine source may then be added followed by addition of the boron compound. In certain instances, such as where boric acid is used in combination with NaOH or another base, water may also be formed from the reaction of boric acid and base. This water may also be removed through heating of the solution. After any drying, the alkoxylating agent may be added. This may be added gradually as the reaction is carried out. The reaction temperatures may be kept at from about ambient to 200° C., with typical reaction temperatures being from about 90° C. to about 150° C. Mixing and heating, if any, may be continued during the reaction.

In certain embodiments, the use of an alcohol that is a non-fluoroalcohol may be used. In such instances, this "stand-in" alcohol is used during catalyst synthesis using the same procedures or steps as with the fluoroalcohol described previously. The fluoroalcohol is then added to the mixture, with the fluoroalcohol displacing the non-fluoroalcohol, such as through evaporation or transesterification. The alcohols are typically low molecular weight alcohols, that have low boiling points so that they can be readily removed, such as through heating and evaporation. When removed in this manner, the volatile alcohols carry away residual water, further drying the reaction mixture. Examples of suitable high volatility alcohols are methanol, ethanol, n-propanol, isopropyl alcohol, butanol, etc. The stand-in alcohol may be used in an amount of from greater than 0 to about 5 mole % or more based on boron. Typically, the stand-in alcohol may be used in an amount of from about 3 mole % to about 4 mole %.

The alkoxylating reaction can be illustrated by the reaction shown in Equations (5) to (8) below:

(5)

(6)

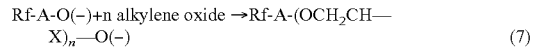
(7)

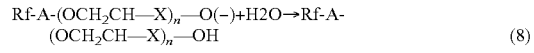
(8)

where Rf is a perfluoroalkyl, such as $F(CF_2)_m$, M is the boron catalyst species, which may or may not carry a formal charge, A is the linking group described from Equation 2, and X may be H or an alkyl group (e.g., —$CH_3$), an alkyl alcohol, an alkyl halide, an aryl, an alkylaryl or an allyl ether, depending on the alkylene oxide used for alkoxylation, and n is an integer, which may range from about 1 to 100 or more. With Equations (5)-(9), certain exchange reactions, for example of a proton or catalyst species, are omitted, but are recognized to occur between various alcohol or alcohol ethoxylate molecules. It should be noted that the linking group A may also be absent from the above equations such as when fluoroalcohols having the structure of Equation 1 are used. The alkoxylated fluoroalcohol may then have the general formula of Equation (9) below:

$$Rf\text{-}(OCH_2CH\text{—}X)_n\text{—}OH \qquad (9)$$

Such alkoxylated fluoroalcohols formed from the above reactions are non-ionic alkoxylated fluoroalcohol products. The alkoxylated fluoroalcohols may also be subsequently derivatized to make anionic fluoroalcohols, such as through the use of, for example, chlorosulfonic acid and phosphorous pentoxide to make ether sulfates and phosphates, respectively, or other products, which may be anionic.

Further processing may be also conducted on the alkoxylated fluoroalcohols, such as catalyst removal, such as by filtration, distillation and other separation techniques. Dilution of the reaction product with solvents, such as water, alcohols, glycols, glycol ethers, etc., and mixtures of the same, may also be used if desired for final products.

The alkoxylated fluoroalcohols prepared in accordance with the invention are useful in formulating paints and coatings, inks, waxes, polishes, anti-corrosion coatings, leveling agents, wetting agents, oil field chemicals, etc.

The method of invention avoids the use of borohydride and boron trifluoride catalysts, while providing the generally the same degree or better reactivity. The boron compounds and other components used in the method of the invention are readily available and generally easily handled and safe to transport and store. Furthermore, resulting alcohols from borate ester transesterification that are formed during the method of the invention may be readily driven off. This is beneficial in that the evaporating alcohols entrain water, which can react with the alkoxylating agent (e.g. ethylene oxide) to produce polyalkylene oxide homopolymers Such polymers provide no useful functionality and give a yield loss and stoichiometric imbalance for the active product. Furthermore, except where NaH is used as the base, no hydrogen gas is evolved, which reduces flammability.

The following examples serve to further illustrate the invention.

EXAMPLES

Example 1

A 139.3 g quantity of a fluoroalcohol having an average molecular weight of about 445 g/mol and the general formula, $F(CF_2)_m$—CH2CH2-OH, was charged to a 4-neck round bottom flask used as the reactor equipped with a mechanical stirrer, septa and a dry ice condenser. To the reactor was added 0.5 g NaOH, which was then heated to 120° C. under a slow nitrogen purge to dissolve the NaOH and dry the fluoroalcohol. Then, 0.6 g iodine and 0.7 g sodium iodide were added as the reactor cooled. At about 50° C., 1.48 ml of trimethyl borate was added, and the reactor was again heated slightly, being held at 60° C. (max.) for 45 min, and then heated again to the reaction temperature of between about 140 and 155° C. Ethylene oxide as added over the course of several hours, with a total of 123.5 g being reacted. The product readily dissolved in water to give a clear, transparent solution and had a surface tension of 22.7 dynes/cm (0.0.227 N/m) at 0.01% w/w. This is contrasted with the starting fluoroalcohol, which had no solubility in water.

Example 2

A 141.3 g quantity of a fluoroalcohol having no solubility in water with the same general formula as that of Example 1 and having an average molecular weight of about 364 g/mol was charged to a reactor as described in Example 1. To the reactor was added 0.7 g NaOH, which was then heated to 125° C. under a nitrogen purge to dissolve the NaOH and dry the fluoroalcohol. Then, 0.7 g iodine and 0.8 g sodium iodide were added as the reactor cooled. At about 50° C., 3.9 ml of triisopropyl borate was added, and the reactor was again heated to 100° C. for 25 min, and then further heated to the reaction temperature of about 140° C. Ethylene oxide was added over the course of several hours between about 130 and 150° C., with a total of 148.7 g being reacted. The final product dissolved in DI water to give a clear, transparent, slightly yellow solution at 1% w/w with a cloud point of 78° C. Upon further dilution with DI water to 0.01% w/w, the solution exhibited a surface tension of 24.6 dynes/cm (0.0246 N/m).

Example 3

The procedures of Example 2 were repeated except that boric acid was used in place of triisopropyl borate. After charging 141.4 g of fluoroalcohol to the reactor, 0.8 g NaOH and 2.6 g boric acid were also added and heated to 125° C. under a nitrogen purge to dissolve the solids and dry the fluoroalcohol. Then, 0.7 g iodine and 0.8 g sodium iodide were added as the reactor cooled. The reactor was heated again to the reaction temperature of about 140° C. Ethylene oxide was added over the course of several hours between about 130 and 150° C., with a total of 55.6 g being consumed. The final product dispersed in DI water to give a hazy, slightly yellow dispersion at 1% w/w. Upon further dilution with DI water to 0.01% w/w, the solution exhibited a surface tension of 17.8 dynes/cm (0.0178 N/m).

While the invention has been shown in some of its forms, it should be apparent to those skilled in the art that it is not so limited, but is susceptible to various changes and modifications without departing from the scope of the invention. Accordingly, it is appropriate that the appended claims should be construed broadly and in a manner to encompass such changes and modifications consistent with the scope of the invention.

I claim:

1. A method of forming an alkoxylated fluoroalcohol comprising combining: at least one boron compound selected from the group consisting of boric acid, boron oxide, a tetraborate salt, and an alkyl borate; iodine; a metal iodide; a base; and a fluoroalcohol together in a mixture,
    whereby the fluoroalcohol reacts with the boron compound to form a borate ester in situ,
    and then subsequently adding an alkylene oxide to the mixture and allowing reactants of the mixture to react to form an alkoxylated fluoroalcohol reaction product.

2. The method of claim 1, wherein the boron compound is an alkyl borate.

3. The method of claim 1, wherein the boron compound is boric acid.

4. The method of claim 1, wherein the boron compound is used in an amount of from about 0.01 mole % to about 20 mole % by total moles of fluoroalcohol.

5. The method of claim 1, wherein the metal iodide is selected from the group consisting of lithium iodide, sodium iodide, potassium iodide, and calcium iodide.

6. The method of claim 1, wherein:
    the fluoroalcohol has the structure $F(CF2)_m$—OH or $F(CF_2)_m$-A-OH, wherein m is from 2 to 20 and A is a

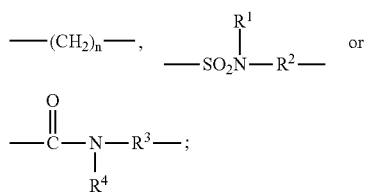 

where n is from 1 to 6, $R^1$ and $R^4$ are each independently selected from the group consisting of hydrogen, a halogen or an alkyl group containing from 1-30 carbon atoms, and $R^2$ and $R^3$ are each independently selected from an alkylene group containing from 2 to 30 carbon atoms.

7. The method of claim 1, wherein: said alkylene oxide has the structure:

$$\begin{array}{c} R^9 \\ R^{10} \end{array} \!\!\!\!\overset{O}{\triangle}\!\!\!\! \begin{array}{c} R^{12} \\ R^{11} \end{array}$$

where $R^9$, $R^{10}$, $R^{11}$ and $R^{12}$ are each independently one of hydrogen, an alkyl group, an alkyl alcohol, an alkyl halide, an aryl, an alkylaryl or an allyl ether.

8. The method of claim 7, wherein said alkylene oxide is ethylene oxide.

9. The method of claim 1 wherein the alkylene oxide is used in an amount of from about 1 mole % to about 100 mole % by total moles of the fluoroalcohol.

* * * * *